United States Patent [19]

Bjornson

[11] 4,205,017
[45] May 27, 1980

[54] HYDRODEHYDROXYLATION PROCESS USING A RHENIUM-FLUORIDED ALUMINA CATALYST

[75] Inventor: Geir Bjornson, Bartlesville, Okla.

[73] Assignee: Phillips Petroleum Company, Bartlesville, Okla.

[21] Appl. No.: 917,045

[22] Filed: Jun. 19, 1978

[51] Int. Cl.² .............................................. C07C 15/00
[52] U.S. Cl. .................................... 585/469; 208/111; 208/112; 252/441; 585/489
[58] Field of Search ............... 260/668 R, 668 D, 669, 260/621; 208/112, 111; 252/441

[56] References Cited

U.S. PATENT DOCUMENTS

| | | | |
|---|---|---|---|
| 2,953,516 | 9/1960 | Gardner | 208/112 |
| 2,998,457 | 9/1961 | Paulsen | 260/621 |
| 3,202,664 | 9/1965 | Brooks et al. | 260/290 |
| 3,236,761 | 2/1966 | Rabo | 208/111 |
| 3,284,513 | 11/1966 | Dedinas et al. | 260/621 |
| 3,707,470 | 12/1972 | Sawa et al. | 260/285 |
| 3,726,810 | 4/1973 | Myers | 252/441 |
| 3,848,019 | 11/1974 | Myers | 260/683.68 |

*Primary Examiner*—Veronica O'Keefe

[57] ABSTRACT

Hydroxy-substituted aromatic compounds are dehydroxylated in the presence of hydrogen and a rhenium-fluorided alumina catalyst at high conversion and selectivity to dehydroxylated aromatic products.

6 Claims, No Drawings

HYDRODEHYDROXYLATION PROCESS USING A RHENIUM-FLUORIDED ALUMINA CATALYST

This invention relates to hydrodehydroxylation of hydroxy-substituted aromatic compounds. In accordance with another aspect, this invention relates to a process for the dehydroxylation of hydroxy-substituted aromatic compounds in the presence of a rhenium-fluorided alumina catalyst. In accordance with a further aspect, this invention relates to a process for converting mixed cresols at high conversion and selectivity to toluene and xylene by contacting with a rhenium-fluorided alumina catalyst under hydrodehydroxylation conditions. In accordance with a further aspect, this invention relates to an improved catalyst comprising rhenium on fluorided alumina which is effective for dehydroxylation of hydroxy-substituted aromatic compounds.

There is an ever-increasing need for aromatic hydrocarbons such as benzene, toluene, and xylene as chemical intermediates and raw materials for a wide range of applications. Benzene, for example, serves as a raw material for styrene, a base material for synthetic rubber and also for dodecylbenzene used in detergents, as well as adipic acid via cyclohexane, and finally as a solvent. Toluene can also be used as a solvent in addition to making explosives (TNT) and as a gasoline additive. Xylene is used as a solvent and as a high quality octane-blending agent for motor fuels. If the present concern with pollution leads to the widespread use of lead-free gasoline, the demand for xylenes as motor fuel could increase more rapidly than the demand for gasoline.

Benzene, toluene, and xylene, referred to as BTX, are obtained principally from petroleum (extractive distillation of catalytically or thermally reformed products and dealkylation processes) or coal (light oil from coke formation and distillation of coal tar).

Coal tar products obtained from coal carbonization or certain fractions from petroleum also contain high amounts of cresols and xylenols which can be dehydroxylated to give BTX provided good economical and efficient processes are found.

Accordingly, an object of this invention is to provide an improved process for dehydroxylation of aromatic compounds.

A further object of this invention is to provide an improved catalyst for hydrodehydroxylation of aromatic compounds.

A further object of this invention is to provide an improved catalyst exhibiting high conversion and selectivity for dehydroxylation of aromatic compounds.

Other objects and aspects, as well as the several advantages of the invention, will be apparent from a study of this disclosure and the appended claims.

In accordance with the invention, hydroxy-substituted aromatic compounds are dehydroxylated by contacting with hydrogen in the presence of a rhenium-fluorided alumina catalyst under dehydroxylation conditions.

In accordance with one specific embodiment of the invention, mixed cresols (o, m, p) are dehydroxylated in the presence of hydrogen at high conversion and selectivity to toluene and xylene by contacting with a rhenium-fluorided alumina catalyst under dehydroxylation conditions.

In accordance with a further embodiment, the invention provides an improved catalyst system of rhenium on fluorided alumina which is effective for hydrodehydroxylation of hydroxy-substituted aromatic compounds.

The catalyst of the invention comprises rhenium, preferably in the form of an oxide deposited on an alumina base containing fluorine. The amount of fluorine in the alumina base is usually from 0.1 to about 80 weight percent of the alumina base, preferably from about 30 to about 70 weight percent. While any alumina can be employed, it is preferred to utilize aluminas having a surface area of at least about 10 square meters per gram, usually about 15 to about 240 square meters per gram. I have found Cristobalite gamma-alumina to be especially suitable.

The fluorine-containing alumina can be prepared, for instance, by treating the alumina with hydrogen fluoride or other fluoride such as ammonium fluoride. In using HF, aqueous HF can be used although treatment is preferably effected with gaseous HF diluted with an inert gas such as nitrogen. Treatment is effected until there is the desired weight percent fluorine found in the catalyst base. The amount of fluorination is roughly proportional to the concentration of HF and the maximum temperature that the fluorination is allowed to reach. The fluoride content increases with both temperature and HF concentration and as the fluoride content of the catalyst increases, the surface area of the catalyst decreases. The alumina is nitrogen purged to remove water and any free fluorine compounds after fluorination.

The method of preparing the catalyst is not a particularly critical feature of this invention, and any known method can be used. However, care must be exercised not to overheat the catalyst prematurely. The rhenium portion of the catalyst system can be deposited on the fluorided alumina carrier through impregnation by an aqueous solution of perrhenic acid $HReO_4$. The catalyst is air dried at ambient room temperature but not heated or placed under vacuum to prevent catalyst component loss. The catalyst is activated by placing it in a tubular reactor in which the hydrodehydroxylation takes place and passing hydrogen through the catalyst for two hours at about 15° C. higher than the temperature at which the hydrodehydroxylation takes place (e.g., 300° to 400° C.). As indicated above, the amount of rhenium, which can be in the form of rhenium oxide, can be broadly about 1 to about 35 weight percent but is preferred to be about 3 to about 25 weight percent, based on the final catalyst composite. The source of rhenium can also be, but not limited to, perrhenate salts having the general formula $MReO_4$ wherein M can be ammonium or a metal from the Groups I, II, or III of the Periodic Table where the valence of M can be $+1$, $+1$, or $+3$. Examples of such metals are lithium, sodium, potassium, rubidium, cesium, beryllium, magnesium, calcium, strontium, barium, boron, aluminum, and gallium, and mixtures thereof. The source of rhenium can also be a mixture of rhenium salts and rhenium acids.

It is generally accepted that after heat activation in the presence of hydrogen, rhenium exists as rhenium oxide (e.g., $Re_2O_7$). Other forms of rhenium such as the free metal are also within the scope of this invention.

The feed for contacting according to the invention can comprise one or more of any aromatic compound having at least one hydroxyl group and includes aromatic compounds that are monocyclic as well as polycyclic. In one embodiment of the invention, the hydroxyl-substituted aromatic compound of the invention is represented by the general formula

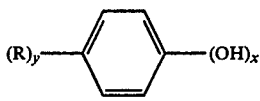

wherein x is 1 to 3, y is 1 to 5, and the sum of x and y is 2 to 6. R is hydrogen or any hydrocarbyl radical including alkyl, cycloalkyl, and aryl radicals having from 1 to 6 carbon atoms. This would include, but not limited to, for example, such materials as phenol, cresols, xylenols, catechol and substituted catechols, resorcinol and substituted resorcinols such as orcinol and n-hexylresorcinol, hydroquinone and substituted hydroquinone, pyrogallol and substituted pyrogallols, phloroglucinol and substituted phloroglucionols, thymol, carvacrol, and the like, and mixtures thereof.

Solvents can be used if so desired and can be, for example, aliphatic, cycloaliphatic, and aromatic hydrocarbons such as hexane, heptane, cyclohexane, benzene, and the like, including mixtures thereof.

Hydrogen is co-mixed with the feed and should always be in a slight molar excess, preferably about 1.5 moles of hydrogen to 1 mole of hydroxy-substituted aryl compounds (e.g., cresol). Any feed rate sufficient for efficient conversion is within the scope of this invention. However, it is generally preferred that the rate be about one LHSV (liquid hourly space velocity), that is, one milliliter of feed per one milliliter of catalyst per hour.

The dehydroxylation conditions of pressure and temperature used in carrying out the instant invention are such that dehydroxylation is effected to remove hydroxy substituents from the aromatic feed at high conversion and high selectivity to dehydroxylated products. However, in general, the conditions of reaction described herein are as follows:

|  |  | Broad Range | Preferred Range |
|---|---|---|---|
| Temperature, | °F. | about 400–1000 | about 600–800 |
|  | °C. | 204–537 | 315–426 |
| Pressre, | psig | about 10–800 | about 450–550 |
|  | MPa | 0.068–5.52 | 3.1–3.79 |

Any type of reactor, but preferably a tubular reactor of stainless steel (e.g., 316) construction, can be employed. The walls of the reactor should be free of material which will interfere with the catalyzed reaction described herein. If desired, the catalyst can be positioned in the reactor near the middle. However, the reaction described herein is very exothermic, and, therefore, it is preferred that the catalyst described herein be admixed with a non-catalytic material such as quartz chips or glass beads in order to effect better mixing and to reduce temperature gradients and hot spots therein.

In the examples, the air-dried catalyst is admixed with an equal volume of an inert material such as quartz chips and placed in the reactor chamber with a bed of inert non-catalytic material above and below the catalyst. With hydrogen gas passing through the system, the catalyst is heated to about 10° to 15° C. above the hydrodehydroxylating temperature of the subsequent catalytic reaction for two hours. The run begins by pressuring the preheated (ca 50° C.) feed through a filter into a Lapp pump and into the top mixing portion of the reactor zone. A static "O" ring switch is set about 100 psi (0.689 MPa) above the operating pressure of the system to protect the pump. Hydrogen is pressured through a Moore backpressure regulator, heated, and mixed with the feed just before entering the mixing head. The hydrogen-feed mixture is passed through the reactor and through a steam-jacketed condenser and Moore backpressure regulator into a chilled receiver. The products can then be analyzed and later separated by distillation.

The following examples serve to illustrate the operability of the current invention.

EXAMPLE I

The invention catalyst composition was prepared as follows: To an aqueous solution comprised of 1.14 grams perrhenic acid, $HReO_4$, and 4.72 grams water were added 28.24 grams of fluorided alumina and mixing gave a just-wet consistency. The catalyst was dried at ambient room temperature. The amount of rhenium deposited on the fluorided alumina is calculated to be about 3 weight percent. The amount of fluorine based on alumina is calculated to be about 33 weight percent. The procedure is repeated until approximately 60 milliliters of catalyst is prepared. Small pieces of catalyst (less than 0.125 in., 0.32 cm), 60 milliliters were placed in the tubular reactor (2.44 cm, 0.96 in. I.D.×70.49 cm, 27.75 in.) herein described and activated by heating to 400° C. for two hours while hydrogen was passed through the system.

EXAMPLE II

A control catalyst system based on rhenium deposited on barium fluoride was prepared as follows: To 51 grams of 9 to 14 mesh size barium fluoride (Harshaw, BA-0201 T) was intimately mixed 2.04 g perrhenic acid, $HReO_4$, and 1.62 milliliters of water. This catalyst was air dried and heat activated in the same manner as described in Example I. The amount of rhenium deposited on barium fluoride is calculated to be about 3 weight percent. The amount of fluoride is calculated to be about 21 weight percent.

EXAMPLE III

To a 316 stainless steel tubular reactor as herein described was charged 60 milliliters of the catalyst and activated as described in Example I. While the temperature was maintained at 371° C. (700° F.) and the pressure at 3.44 MPa (500 psi), an equimolar ratio of ortho, meta, and para cresol was fed through the reactor at a rate of about 55 to 60 milliliters per hour (1.0 LHSV), the pressure being maintained by hydrogen which mixes with the cresol feed at a molar ratio of about 1.5 moles of hydrogen to 1 mole of cresol feed. The effluent product was analyzed without further separation with a Bendix ® 2300 chromatograph employing a column comprised of 12 weight percent 6-ringed polyphenyl ether on Chromasorb G, 80-100 mesh, which had been previously acid washed and dimethylsiliconized. The column was programmed as follows: 100° C. to 190° C. at 30° C./min.; 190° C. to 250° C. at 10° C./min.; and isothermal at 250° C. until complete. Analysis indicated an 85.6 percent conversion with a product selectivity (distribution) of 0.59 percent phenol, 89.59 percent BTX (benzene, toluene, xylene of which 82.65 percent was toluene), 6.52 percent xylenols, and 3.30 percent unknowns. The run was repeated at 482° C. (900° F.) to give an 86.74 percent conversion with a product distribution of 3.84 percent phenol, 90.49 percent BTX (82.6 percent is toluene), 4.68 percent xylenols, and 0.99 percent unknowns.

EXAMPLE IV

The run described in Example III was repeated at 371° C. (700° F.) except the feed was 2,4-xylenol(2,4-dimethylphenol). Analysis indicated a 75 percent conversion with a product distribution of 0.41 percent phenol, 89.69 percent BTX (1.1% benzene, 13.8% toluene, 70.2% m-xylene), 3.88 percent cresols, 6.01 percent unknowns.

EXAMPLE V

The rhenium on barium fluoride catalyst described in Example II was used for comparison purposes to convert an equimolar feed of ortho, meta, and para cresols in the manner herein described. The conversion at 371° C. (700° F.) was 34.2 percent with a product distribution of 4.11 percent phenol, 87.27 percent BTX, 2.48 xylenols, and 6.13 percent unknowns. At 482° C. (900° F.) the conversion was 48.2 percent with a product distribution of 17.37 percent phenol, 57.5 percent BTX, 13.46 percent xylenols, and 11.68 percent unknowns.

EXAMPLE VI

An equimolar quantity of ortho, meta, and para cresol was treated in a similar manner herein described but employed as an alternate comparison catalyst system, Girdler 41 which is an eleven weight percent chromium on alumina catalyst. Analysis indicated that at a reaction temperature of 371° C. (700° F.) the conversion was 39.3 percent with a product distribution of 51.81 percent phenol, 1.42 percent BTX, 43.49 percent xylenols, and 3.28 percent unknowns.

The following table summarizes the data herein disclosed.

TABLE I
Summary of Data

| EXAMPLE | Catalyst | Temperature °C. | °F. | % Conversion | % SELECTIVITY Phenol | BTX$^a$ | Xylenols | Unknown |
|---|---|---|---|---|---|---|---|---|
| 1. Cresol Feed | | | | | | | | |
| III | Re/F$_2$-Al$_2$O$_3$ | 371 | 700 | 85.65 | 0.59 | 89.59$^b$ | 6.52 | 3.30 |
| III | | 482 | 900 | 86.74 | 3.84 | 90.49$^b$ | 4.68 | 0.99 |
| V | Re/BaF$_2$ | 371 | 700 | 34.20 | 4.11 | 87.27 | 2.48 | 6.13 |
| V | | 482 | 900 | 48.20 | 17.37 | 57.50 | 13.46 | 11.68 |
| VI | Cr/Al$_2$O$_3$ | 371 | 700 | 39.30 | 51.81 | 1.42 | 43.49 | 3.28 |
| 2. 2,4-Xylenol Feed | | | | | | | | |
| IV | Re/F$_2$-Al$_2$O$_3$ | 371 | 700 | 75.00 | 0.41 | 89.69$^c$ | 3.88$^d$ | 6.01 |

$^a$BTX = benzene, toluene, xylene.
$^b$82.65 percent toluene.
$^c$1.1 percent benzene, 13.8 percent toluene, 70.2 percent m-xylene.
$^d$Cresols.

The above data indicate that the inventive catalyst system rhenium on fluorided alumina is a superior catalyst compared to another rhenium on a metal fluoride base and a chromium on alumina support. This superiority is based on the significant increase in conversion which is about twice the value of the two control runs. In addition, the amount of phenol formed is less with the inventive catalyst than with the controls.

Although the conversion is slightly less, the inventive catalyst gives about the same product selectivity with 2,4-xylenol(2,4-dimethylphenol) and should work equally well with any type hydroxy or polyhydroxy aryl or substituted aryl compound.

In Example I, the fluorided alumina was prepared in accordance with the following procedure. 7.5 Pounds of ⅛-inch Cristobalite gamma Al$_2$O$_3$ tablets were placed in a tubular 3-inch diameter stainless steel reactor fitted with an aluminum liner (2.75 inch I.D. ×45 inches) and heated to about 220° F. (104° C.). A stream of nitrogen is passed over the surface of liquid HF at ambient room temperature and the N$_2$/HF stream passed through the reactor containing Al$_2$O$_3$ at about 30 psig. The absorption of HF on the alumina surface is exothermic so care was exercised to maintain a steady increase in temperature. The rate of the N$_2$/HF stream was controlled so that the temperature within the reactor did not exceed 600° F. (316° C.). After about 11 hours, the N$_2$/HF stream was stopped, the fluorided alumina cooled and analyzed. Analysis indicated 33 weight percent fluoride ion and a surface area of 141 m$^2$/gm. During this run approximately 2.5 pounds of HF had been nitrogen swept over the alumina.

I claim:

1. A hydrodehydroxylation process which comprises contacting at least one substituted aromatic compound having at least one hydroxyl group with hydrogen in the presence of a catalyst consisting essentially of rhenium and fluorided alumina under hydrodehydroxylation conditions sufficient to dehydroxylate at least one of said aromatic compounds and produce dehydroxylated products at high conversion and high selectivity.

2. A process according to claim 1 wherein the aromatic compound has the general formula

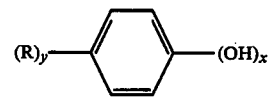

wherein x is 1 to 3, y is 1 to 5, and the sum of x and y is 2 to 6, and R is hydrogen or a hydrocarbyl radical having from 1 to 6 carbon atoms.

3. A process according to claim 1 wherein the temperature of contacting is in the range of about 400°-1000° F. (204°-537° C.) and 10-800 psig (0.068-5.52 MPa) and the amount of rhenium in the catalyst ranges from 1-35 weight percent, based on the total catalyst composite, and the amount of fluorine present is in the range of 0.1 to about 80 weight percent of the alumina.

4. A process according to claim 1 wherein the feed for said contacting comprises ortho cresol, meta cresol, and para cresol.

5. A process according to claim 1 wherein the feed for said contacting comprises 2,4-xylenol and the temperature of contacting is in the range of from about 600°-800° F. (315°-426° C.).

6. A process according to claim 1 wherein the feed for said contacting comprises a mixture of ortho, meta, and para cresol and the temperature is in the range of about 600°-800° F. (315°-426° C.).

* * * * *